(12) United States Patent
Oonuki et al.

(10) Patent No.: US 7,798,972 B2
(45) Date of Patent: Sep. 21, 2010

(54) PUNCTURE ADAPTER AND AN ULTRASONIC PROBE, AND THE METHOD OF USING THE SAME

(75) Inventors: Yutaka Oonuki, Otawara (JP); Susumu Hiki, Otawara (JP); Hiroyuki Shikata, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 353 days.

(21) Appl. No.: 11/843,333

(22) Filed: Aug. 22, 2007

(65) Prior Publication Data

US 2008/0064962 A1    Mar. 13, 2008

(30) Foreign Application Priority Data

Sep. 7, 2006    (JP) .............................. 2006-242749

(51) Int. Cl.
*A61B 8/00* (2006.01)
*A61B 8/14* (2006.01)
(52) U.S. Cl. ...................................... 600/464; 600/567
(58) Field of Classification Search .................. 600/461, 600/464, 462
See application file for complete search history.

(56) References Cited

U.S. PATENT DOCUMENTS

| | | | | |
|---|---|---|---|---|
| 4,469,106 A | * | 9/1984 | Harui | 600/461 |
| 4,883,059 A | * | 11/1989 | Stedman et al. | 600/437 |
| 5,076,279 A | * | 12/1991 | Arenson et al. | 600/461 |
| 5,792,059 A | * | 8/1998 | Furia et al. | 600/459 |
| 5,931,787 A | * | 8/1999 | Dietz et al. | 600/461 |

FOREIGN PATENT DOCUMENTS

| | | |
|---|---|---|
| JP | 5-137732 | 6/1993 |
| JP | 6-189974 | 7/1994 |
| JP | 2000-342587 | 12/2000 |

* cited by examiner

*Primary Examiner*—Eric F Winakur
*Assistant Examiner*—Helene Bor
(74) *Attorney, Agent, or Firm*—Oblon, Spivak, McClelland, Maier & Neustadt, L.L.P.

(57) ABSTRACT

A puncture adapter is provided for being mounted on an ultrasonic probe. The ultrasonic probe to be mounted comprises a rod-like insertion portion that is insertable into a subject and has a search unit for transmitting and receiving ultrasonic waves at the tip end of the insertion portion, and in which a guide channel for guiding a puncture needle is formed on a side surface of the insertion portion. This puncture adapter has a first tubular component on which a gap is provided on a side surface along the length direction, which gap is from one end to the other side of the side surface. The first tubular component is mounted so as to contact the outside of the insertion portion and cover the guide channel, and is turnable in the circumferential direction thereof.

8 Claims, 7 Drawing Sheets

PUNCTURE ADAPTER AND AN ULTRASONIC PROBE, AND THE METHOD OF USING THE SAME

BACKGROUND OF THE INVENTION

1. Field of the Invention

The present invention relates to a puncture adapter to be mounted on an ultrasonic probe and an ultrasonic probe consisting of an ultrasonic probe body and a puncture adapter. This ultrasonic probe is used for puncturing by piercing a puncture needle into a subject to extract tissue from an affected area or treat tissue, and particularly by inserting an insertion portion including an ultrasonic transducer into a living body.

2. Description of the Related Art

Conventionally, puncturing by piercing a puncture needle such as injection needle into a living body, have been performed. The puncturing are intended for examinations extracting tissue such as a tumor, local administration of a medical agent, or hyperthermia therapy such as irradiation by microwaves or radio waves from the puncture needle. Such puncturing is typically performed with reference to a tomographic image generated by an ultrasonic diagnostic device in order to avoid a blood vessel at the risk of causing massive hemorrhaging due to injury, or in order to accurately puncture a tissue such as a tumor that is an object of observation.

Meanwhile, as described in Japanese Unexamined Patent Application Publication H6-189974, in laparoscopic surgeries, puncturing is performed whereby an insertion portion comprising a line of ultrasonic transducers on the tip end is inserted and a tomographic image is referenced as described above.

In addition, in the abovementioned puncture, the ultrasonic probe and the puncture needle are washed, because they are stained with blood. However, as described in Japanese Unexamined Patent Application Publication H6-189974, when integrated with a puncture needle, it is difficult to wash the puncture needle and the ultrasonic probe.

In addition, while hyperthermia therapy is performed by irradiation of microwaves or radio waves employing a puncture needle after piercing with the puncture needle, it is not easy to separate from the puncture needle to observe a target site from another direction. Therefore, an operator such as a physician has to hold the ultrasonic probe by some means. To release the ultrasonic probe in such a case, it is desirable to detach the ultrasonic probe from the puncture needle and to retrieve the ultrasonic probe from the living body.

Therefore, an ultrasonic probe comprising a guide channel for guiding a puncture needle is employed. FIG. 1 shows a conventional ultrasonic probe 1. The ultrasonic probe 1 is provided with a substantially cylindrical grip 13 for being grasped by an operator, the grip 13 is connected to a cable 15 at one end thereof, and a rod-like insertion portion 10 is extended in the identical direction toward the axial direction of the grip 13 at the other end. In addition, the tip of the insertion portion 10 comprises a transducer array (not shown) for transmitting and receiving ultrasonic waves. Then, a guide channel 11 for guiding the puncture needle in the axial direction of the insertion portion 10 is provided on the surface of the rod-like insertion portion on the tip end of the insertion portion 10. In addition, a guideline 12 that is a marker of the position of the guide channel 11 is formed in the grip 13 direction from the end on the grip 13 side of the guide channel 11.

In addition, a brief overview of puncturing with the use of a ultrasonic probe 1 in laparoscopic surgery is shown in FIG. 2. As shown in FIG. 2, the abdominal wall is elevated upward by a heretofore known pneumoperitoneum, lifting method, or the like, to establish a space between organs and the abdominal wall. Then, several holes with a diameter of approximately 5 to 10 mm are created in the abdominal area, into which a trocar is inserted. In addition, a laparoscope or an endoscope is provided in the space, so the internal abdominal area is displayed on a TV monitor as a video picture. Then, the ultrasonic probe 1 is inserted into the living body through the trocar. Then, after a tomographic image is displayed on the TV monitor, the puncture needle 2 is inserted into the living body from another trocar, and the tip of the puncture needle 2 is placed in the guide channel 11 on the tip end of the ultrasonic probe 1 and pierced in the direction of the affected area along the guide channel 11. Then, hyperthermia therapy by irradiation of microwaves or radio waves is performed. At this time, the puncture needle 2 is merely placed in the guide channel 11, so it is possible to easily detach the ultrasonic probe 1 from the puncture needle 2. In addition, the guide channel 11 can be easily washed, because it has an aperture shape.

In addition, also in operative treatments which are performed by making an approximate one-inch incision, the guide channel of the insertion portion of the ultrasonic probe is similarly employed, though the length of the insertion portion is shorter than that employed in laparoscopic surgery.

However, when piercing with the puncture needle as described above along the guide channel, it is difficult to keep the puncture needle stable, so the puncture needle may become detached from the guide channel if force is applied to the puncture needle to let it move in the direction of the aperture of the guide channel. In particular, when an operator is not used to operation, the operator may detach the puncture needle from the guide channel during operation.

In addition, the puncture needle may be inserted from a trocar into which an ultrasonic probe is inserted, being guided by the trocar. For that, the trocar with an inner diameter close to the diameter of the insertion portion of the ultrasonic probe is employed. However, when the trocar with an inner diameter close to the diameter of the insertion portion cannot be used, the difference in diameter from the insertion portion is large, so it is not possible to guide the puncture needle. Furthermore, in the pneumoperitoneum performed by injecting gas into the abdominal area for inflation, air leaks from the gap between the diameters. In addition, even when employing one with a small difference in diameter with the insertion portion, the length of a trocar is normally short, as shown in FIG. 2. Therefore, in the proximity of the tip of the ultrasonic probe, the puncture needle is difficult be guided by the trocar, resulting in deviation of the piercing direction.

SUMMARY OF THE INVENTION

A first aspect of the present invention is: a puncture adapter mounted on an ultrasonic probe, the ultrasonic probe comprising a rod-like insertion portion that is insertable into a subject, and a search unit for transmitting and receiving ultrasonic waves at the tip end of the insertion portion, wherein a guide channel for guiding a puncture needle is formed on a side surface of the insertion portion, wherein a first tubular component is provided on which a gap is provided on a side surface thereof along the length direction, the gap being from one end to the other side of the side surface, and the first tubular component is mounted so as to contact the outside of the insertion portion and cover the guide channel, and is turnable in the circumferential direction thereof.

A second aspect of the present invention is: an ultrasonic probe consisting of an ultrasonic probe body and a puncture adapter, wherein the ultrasonic probe body comprises a rod-like insertion portion that is insertable into a subject and has a search unit for transmitting and receiving ultrasonic waves at the tip end of the insertion portion, and in which a guide channel for guiding a puncture needle is formed on a side surface of the insertion portion, and the puncture adapter has a first tubular component on which a gap is provided on a side surface thereof along the length direction, the gap being from one end to the other side of the side surface, and the first tubular component is mounted so as to contact the outside of the insertion portion and cover the guide channel, and is turnable in the circumferential direction thereof.

A third aspect of the present invention is: a method for mounting a puncture adapter composed of tubular components on which a gap is provided along the length direction, the gap being from one end to the other side, on an ultrasonic probe comprising a rod-like insertion portion that is insertable into a subject and having a search unit for transmitting and receiving ultrasonic waves at the tip end of the insertion portion, the ultrasonic probe in which a guide channel for guiding a puncture needle is formed on a side surface of the insertion portion, the method comprising: being embedded on the outside of the insertion portion from the gap of the tubular component, turning in the circumferential direction of the insertion portion to shift the positions of the gap and the guide channel so as to cover the guide channel, allowing the puncture needle to pass through from the guide channel covered with the tubular component, and turning in the circumferential direction of the insertion portion after the puncture needle reaches a target area, to match the gap and the guide channel so that the puncture needle is detached from the guide channel.

DETAILED DESCRIPTION OF THE EMBODIMENTS

Reference will now be made in detail to the present embodiments of the invention, examples of which are illustrated in the accompanying drawings.

First Embodiment

Figure 3:
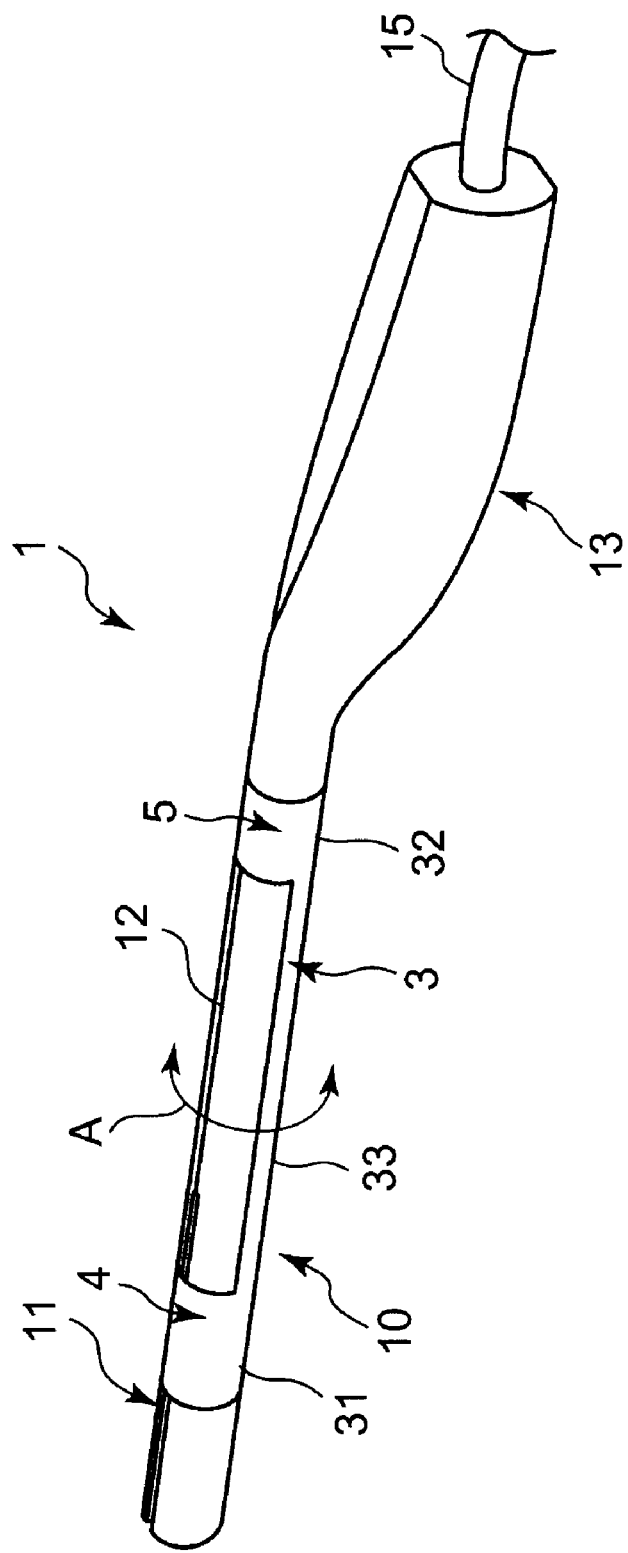
FIG. 3 is a perspective view showing the appearance of an ultrasonic probe on which a puncture adapter is mounted in the first embodiment.

FIG. 3 shows the appearance of the ultrasonic probe 1 on which the puncture adapter 3 is mounted in the first embodiment. As shown in FIG. 3, the puncture adapter 3 is mounted on the insertion portion 10 of the ultrasonic probe 1. In addition, the ultrasonic probe body of the present invention is explained by means of the ultrasonic probe 1.

Figure 4:
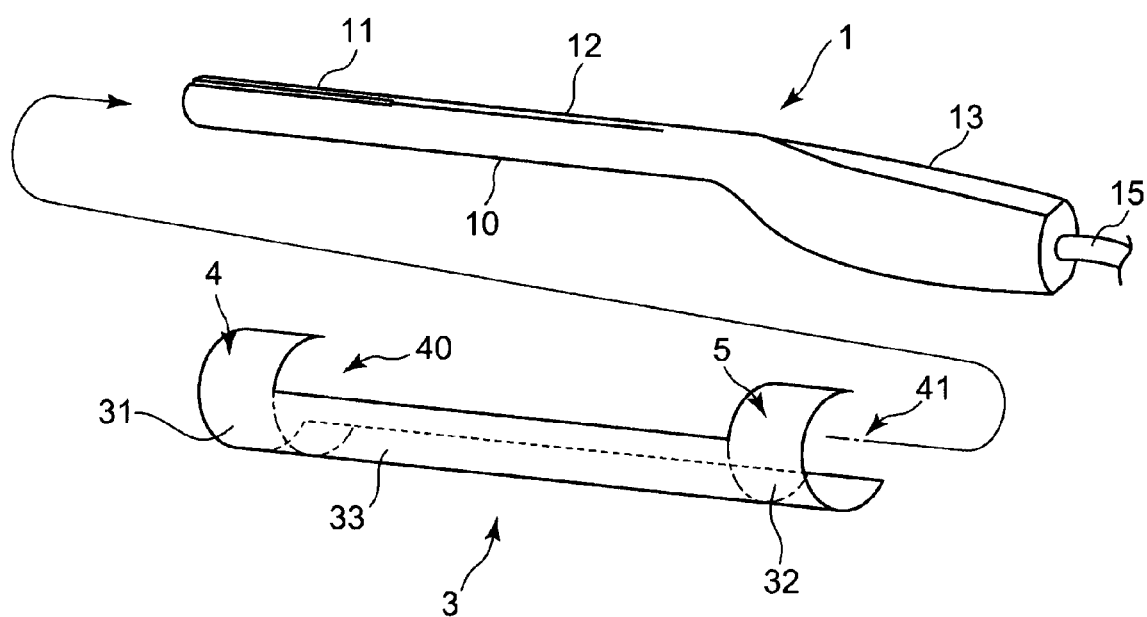
FIG. 4 is a perspective view of a puncture adapter in a first embodiment and of an ultrasonic probe on which the puncture adapter is to be mounted.

FIG. 4 is a perspective view that shows the ultrasonic probe 1 and puncture adapter 3. The ultrasonic probe 1 shown in FIG. 4 is employed in laparoscopic surgery by insertion into a living body. Herein, each portion of the ultrasonic probe 1 and puncture adapter 3 is explained by means of FIG. 4.

The ultrasonic probe 1, as shown in FIG. 4, is provided with a substantially cylindrical grip 13 for being grasped by an operator, the grip 13 is connected to a cable 15 at one end thereof, and a rod-like insertion portion 10 is extended in the identical direction toward the axial direction of the grip 13 at the other side. The tip of the insertion portion 10 comprises a transducer array (not shown) for transmitting and receiving ultrasonic waves. Then, a guide channel 11 for guiding the puncture needle 2 (not shown) along the axial direction of the insertion portion 10 is provided on the surface of the rod-like insertion portion on the tip end of the insertion portion 10. This guide channel 11 is provided from the tip end of the insertion portion 10 to the intermediate portion in the axial direction of the insertion portion 10. On the terminating end of this guide channel 11, the guideline 12 is formed so as to be along the grip 13 direction and indicates the circumferential position of the guide channel 11.

The puncture adapter 3 has a tubular component (cylindrical component) on which a gap is provided on a side surface along the length direction, the gap from one end to the other side of the side surface. This tubular component has a circular cross-section, and a cutout occurs in a portion of this cross-section by providing a gap. This tubular component is mounted so as to contact the outside of the insertion portion 10 and cover the guide channel 11, and is turnable in the circumferential direction thereof. When it is mounted, the ultrasonic probe 1 and the puncture adapter 3 may be in close contact with each other, or may be slightly displaced from each other. In order to smoothly turn the puncture adapter 3, the outside of the ultrasonic probe 1 or the inside of the puncture adapter 3 may be composed of materials that have low friction.

The puncture adapter 3, as shown in FIG. 4, is provided with a guide portion 4 to be employed for guiding the puncture needle 2 (not shown) on one end, and the operating portion 5 to be operated by an operator pinching it when turning the puncture adapter 3 on the other end. In addition, the guide portion 4 and operating portion 5 of the puncture adapter 3 are coupled at the coupling portion 33 and integrated with each other. Moreover, the boundary among the guide portion 4, the operating portion 5, and the coupling portion 33 is indicated by a dashed-dotted line in FIG. 4, but this is only to illustrate the boundary in the figure, and is not actually depicted.

The width of this gap can be wider than or equal to the guide channel. Then, the tubular component can detach the puncture needle 2 from the guide channel 11 when the guide channel 11 is placed into the gap by turning in the circumferential direction, and confines the puncture needle 2 within the guide channel 11 when the guide channel 11 deviates from the gap.

The guide portion 4 consists of a tubular component 31 (first tubular component) having almost circular openings. The guide portion 4 is provided with a gap 40 that leads to the openings from the outside, the gap being from one end to the other end of the tubular component 31, and the circumferential direction of the tubular component 31 is noncontiguous due to the gap 40. The width of the gap 40 only has to be at least the width of the guide channel 11 of the ultrasonic probe 1. Herein, "the nearly circular openings" refer to openings having a gap 40 in which the circumferential direction is noncontiguous in this way. In other words, the cross-section of the tubular component 31 is C-shaped.

The operating portion 5 consists of a tubular component 32 (second tubular component) having almost circular openings, as is the case with the guide portion 4. Gap 41 leading to the openings from the outside is provided from one end to the other end of the tubular component 32, and causes non-contiguous figure of the tubular component 32 in the circumferential direction. At the operating portion 5, the width of the gap 41 is not defined by the guide channel 11. In addition, the cross-section of the tubular component 32 is C-shaped, as with the guide portion 4.

The coupling portion 33 consists of a gutter-shaped body for coupling the opposing ends of the guide portion 4 and the operating portion 5. The coupling portion 33, as the shape of a gutter, is configured as a straight line in the length direction and a curved line in the width direction to be formed into the gutter-shaped body. In addition, the gutter-shaped body has the same curvature as that of the tubular component with which it is to be coupled.

In addition, the puncture adapter 3 is formed as shown in FIG. 4 by fabricating one material to form the guide portion 4, the operating portion 5 and the coupling portion 33. For example, the material may be a metal plate such as titanium or stainless steel. Employing such metal plates produces a tightening force due to the springy characteristics, and the tightening force allows the puncture adapter 3 to be mounted. At this time, the inner diameter of the respective tubular components 31 and 32 of the guide portion 4 and the operating portion 5 may be fabricated smaller than the outer shape of the mounted partner (the insertion portion 10 of the ultrasonic probe 1 that will be described later in the present example). In this case, the inner diameter stretches out and consequently returns, so a tightening force will be produced.

In addition, the puncture adapter may be formed by employing not only a metal plate but also resin. In case of resin, the springy characteristics of the resin allows the puncture adapter 3 to be mounted. The outer shape of the tubular component is not limited to a circular cross-section but may be a polygonal shape.

In addition, as shown in FIG. 4, for example, the insertion portion 10 of the ultrasonic probe 1 is inserted into the puncture adapter 3 from the tip side so that the puncture adapter 3 is mounted on the ultrasonic probe 1. Next, the puncture adapter 3 is mounted so that the operating portion 5 is on the backside of the insertion portion 10, i.e., on the grip 13 side, and the guide portion 4 is arranged on the tip end of the insertion portion 10 and covers a portion of the guide channel 11.

In addition, as described above, the puncture adapter 3 contacts the insertion portion 10 by the tightening force due to the springy characteristics of the tubular component 31 of the guide portion 4 and the tubular component 32 of the operating portion 5, and is mounted by the tightening force. Therefore, a frictional force produced by the tightening force, for example, is applied in the circumferential direction (direction of the arrow A) of the insertion portion 10 to the puncture adapter 3 that has been mounted, to allow the puncture adapter 3 to easily turn. In other words, the puncture adapter 3 is turnably mounted in the circumferential direction of the insertion portion 10.

In addition, in order to position the puncture adapter 3 in the axial direction of the insertion portion 10, for example, a protrusion (not shown) may be provided on the grip 13 side of the insertion portion 10 so that the protrusion is struck, or a bump (not shown) may be provided that lowers the position on which the puncture adapter 3 is mounted so that the puncture adapter 3 may fit into the bump.

Figure 5A:
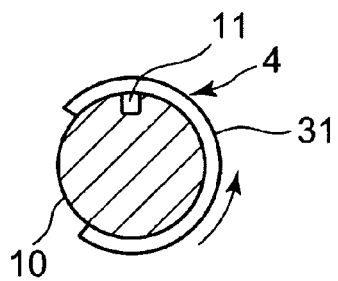
FIGS. 5A and 5B are cross-sectional views showing an ultrasonic probe when turning the puncture adapter in various different directions.
Figure 5B:
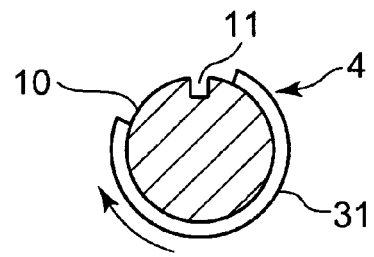

FIG. 5 shows an ultrasonic probe when turning the puncture adapter 3 in the circumferential direction of the insertion portion 10. FIG. 5A shows a cross-sectional view when turning the puncture adapter 3 counterclockwise as viewed from the tip end of the insertion portion 10. As shown in FIG. 5A, the guide channel 11 is covered with the tubular component 31 of the guide portion 4 so that the guide channel 11 and the tubular component 31 form a guide opening. At this shielded position, the puncture adapter 3 confines the puncture needle 2 within the guide channel 11. FIG. 5B shows a cross-sectional view when turning the puncture adapter 3 clockwise as viewed from the tip end of the insertion portion 10. As shown in FIG. 5B, the aperture area of the guide channel 11 is opened. At this open position, the puncture adapter 3 allows the puncture needle 2 to be detached from the guide channel 11. In addition, in order to position the puncture adapter 3 for turning in the circumferential direction, for example, a protrusion (not shown) or a bump (not shown) may be provided on the insertion portion 10 so as to strike it when turning.

Figure 6A:
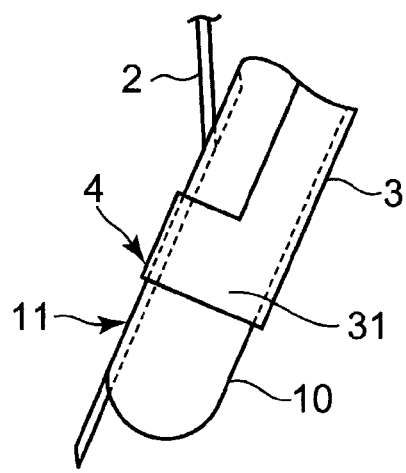
FIGS. 6A and 6B are views that show an ultrasonic probe when turning the puncture adapter in various different directions and showing the puncture needle in each case.
Figure 6B:
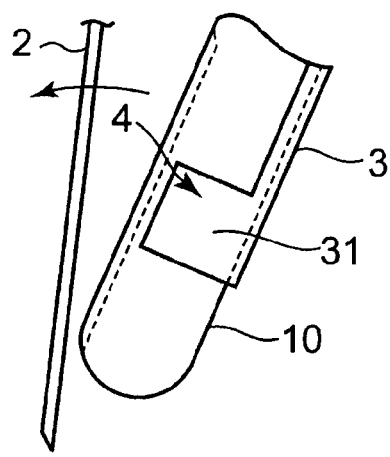

FIGS. 6A and 6B show side views of the puncture adapter 3 turned in the circumferential direction of the insertion portion 10. Operations of a puncture needle in the inserted state and the separated state are explained by means of FIG. 6. FIG. 6A is a side view of the puncture adapter 3 turned to the position in FIG. 5A. In other words, FIG. 6 shows an ultrasonic probe guiding in laparoscopic surgery the puncture needle 2 with the puncture adapter 3 of the present embodiment. As shown in FIG. 6A, the puncture needle 2 is guided along the guide channel 11, passes through the guide opening formed by the guide channel 11 and the tubular component 31 of the guide portion 4, and is further guided along the guide channel 11. At this time, even if force is applied to the puncture needle 2 to let it move in the direction of the aperture of the guide channel 11, the puncture needle 2 is never detached from the guide channel 11, because the tubular component 31 covers the guide channel 11. FIG. 6B is a view of the puncture adapter 3 of the present embodiment guiding the puncture needle 2 in laparoscopic surgery, and turning to the position of FIG. 5B. As shown in FIG. 6B, the aperture area of the guide channel 11 is opened to allow the puncture needle 2 to be detached, and it is possible to leave only the piercing puncture needle 2 by removing the ultrasonic probe 1. In addition, it is possible to treat while piercing with only the puncture needle 2. Moreover, The ultrasonic probe 1 can be employed in another portion.

Figure 1:
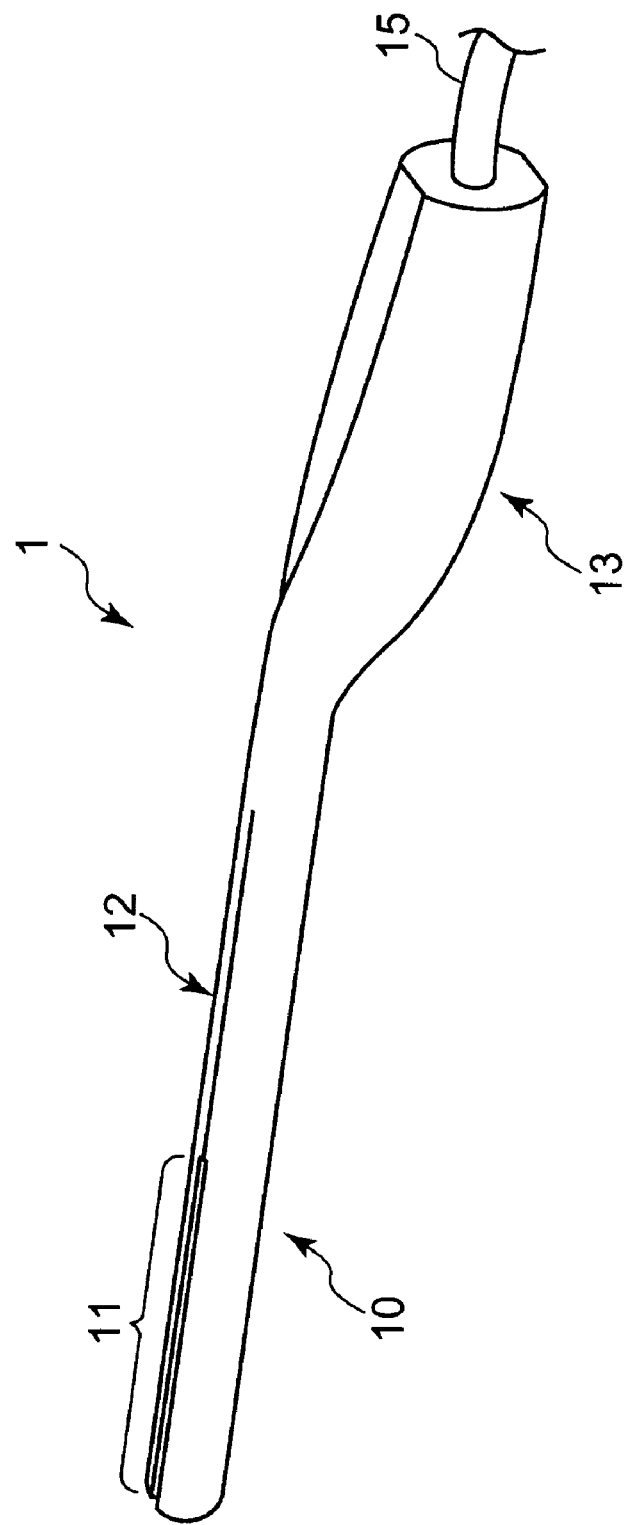
FIG. 1 is a perspective view of a conventional ultrasonic probe.
Figure 2:
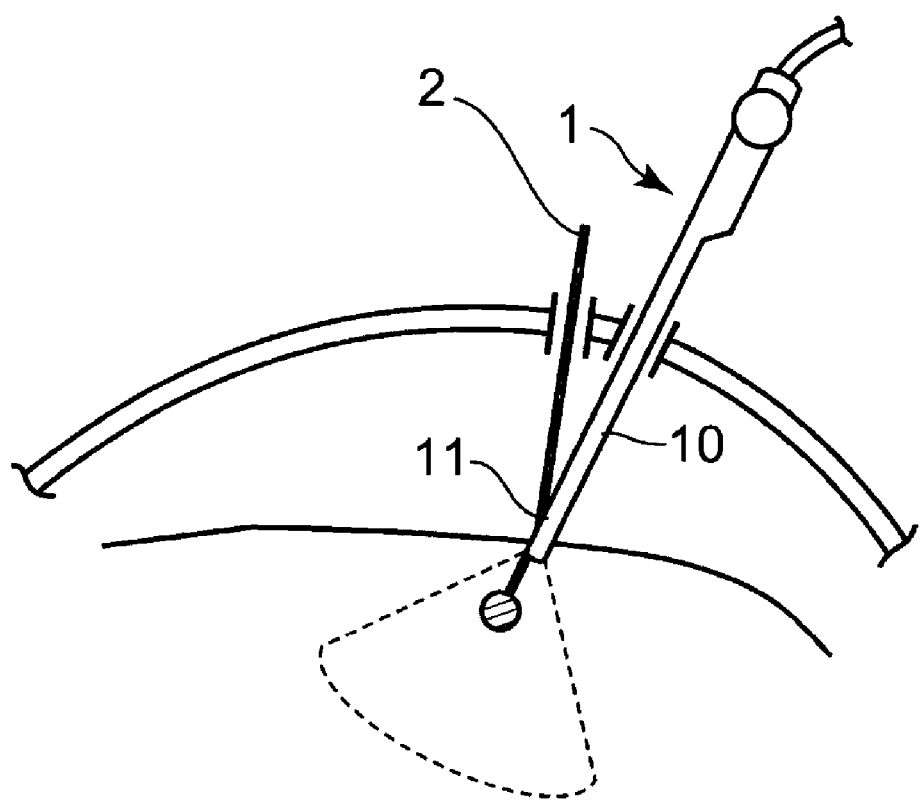
FIG. 2 is an explanatory diagram of usage of the present ultrasonic probe in conventional laparoscopic surgery.
Figure 7:
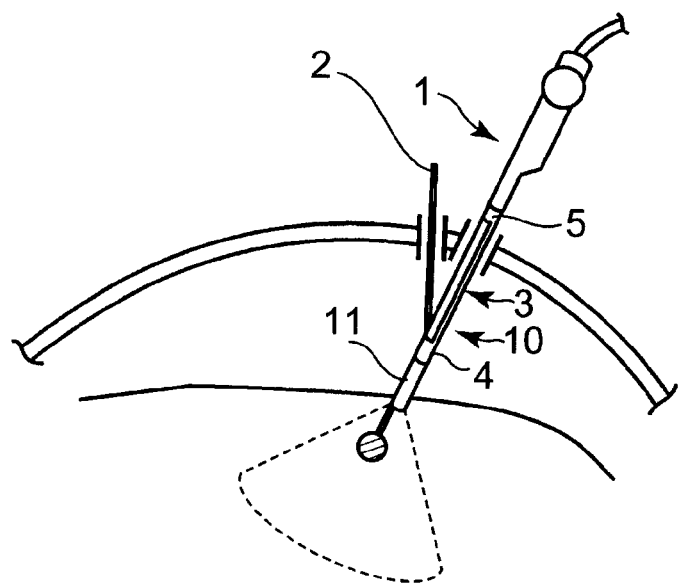
FIG. 7 is an explanatory diagram of usage of the present ultrasonic probe in laparoscopic surgery.

FIG. 7 is an explanatory diagram for explaining usage of the present ultrasonic probe 1 in laparoscopic surgery. Herein, usage of the present puncture adapter 3 in case of puncturing in laparoscopic surgery is explained in further detail by means of FIG. 7. As shown in FIG. 7, the abdominal wall is elevated upward by a heretofore known pneumoperitoneum or lifting method to establish a space between organs and the abdominal wall. Then, several holes with diameters approximately 5 to 10 mm are created in the abdominal area, into which a trocar is inserted. In addition, although not shown, a laparoscope or an endoscope is provided in the space, so the internal abdominal area is displayed on a TV monitor as a video picture. Meanwhile, an ultrasonic probe 1 and a puncture adapter 3 are prepared. This puncture adapter 3 consists of tubular components as shown, for example, in FIG. 2, which are provided with a gap along the length direction from one end to the other end.

First, the puncture adapter 3 is mounted on the ultrasonic probe 1 by embedding the same on the outside of the insertion portion 10 from this gap of the tubular component. Then, the position of the gap is shifted to cover the guide channel 11 by turning the puncture adapter 3 in the circumferential direction of the insertion portion 10. Next, the ultrasonic probe 1 is inserted into a trocar as shown in FIG. 5A. Then, after a tomographic image is displayed on the TV monitor, the puncture needle 2 is inserted from another trocar. At this time, the position of the puncture adapter 3 is fixed to the position of the insertion portion 3 to allow the puncture needle 2 to pass through from the guide channel 11 covered with the tubular component. Then, the tip of the puncture needle 2 is placed so as to be along the guide channel 11 on the near side of the guide portion 4, further allowing it to pass through the guide opening formed by the guide channel 11 and the tubular component 31 of the guide portion 4, and further piercing in the direction of the affected area along the guide channel 11.

Next, after the puncture needle 2 reaches the affected area that is a target position, the puncture adapter 3 is turned in the circumferential direction of the insertion portion 3 to match the gap and the guide channel 11 each other so that the puncture needle 2 is detached from the guide channel 11. Herein, when the operating portion 5 is outside the trocar as shown in FIG. 7, an operator pinches the operating portion 5, turns the same in the circumferential direction of the insertion portion 10 as shown in FIG. 5B, and opens the guide channel 11. Meanwhile, although not shown, when the operating portion 5 of the puncture adapter 3 is inside the trocar, the operator inserts a clamp via the trocar, pinches the operating portion 5 or the guide portion 4 within the abdominal area using the clamp and turns the same in the circumferential direction of the insertion portion 10 as shown in FIG. 5B to open the guide channel 11. Then, the puncture needle 2 is detached from the ultrasonic probe 1 to perform hyperthermia therapy by irradiation of microwaves or radio waves while only the puncture needle 2 remains to pierce the tissue.

In this explanation, while the puncture adapter 3 is premounted on the ultrasonic probe 1 and is inserted from the trocar, it can also be mounted inside the abdominal area in laparoscopic surgery.

Moreover, when repeating the above treatment, the formation of a guide opening and the opening of the guide channel can be repeated by turning the puncture adapter 3, so it is not necessary to repeatedly mount and attach the puncture adapter 3.

Figure 8:
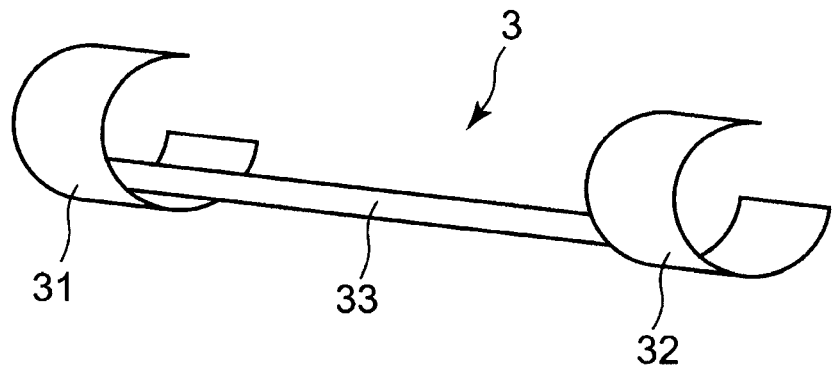
FIG. 8 is a perspective view showing a puncture adapter with a structure different from the puncture adapter shown in FIG. 4.

FIG. 8 is a perspective view of a puncture adapter with a structure different from the puncture adapter shown in FIG. 4. While FIG. 4 shows a puncture adapter created from one sheet of metal, as shown in FIG. 8, it is also possible to create it such as by welding to fix two tubular components 31 and 32 created as independent bodies to both ends of the coupling portion 33 further created as an independent body. In addition, also in the case of the ultrasonic probe to be employed in so-called one-inch surgery, it is possible to puncture by mounting the puncture adapter as described above into the insertion portion thereof.

Second Embodiment

Figure 9:
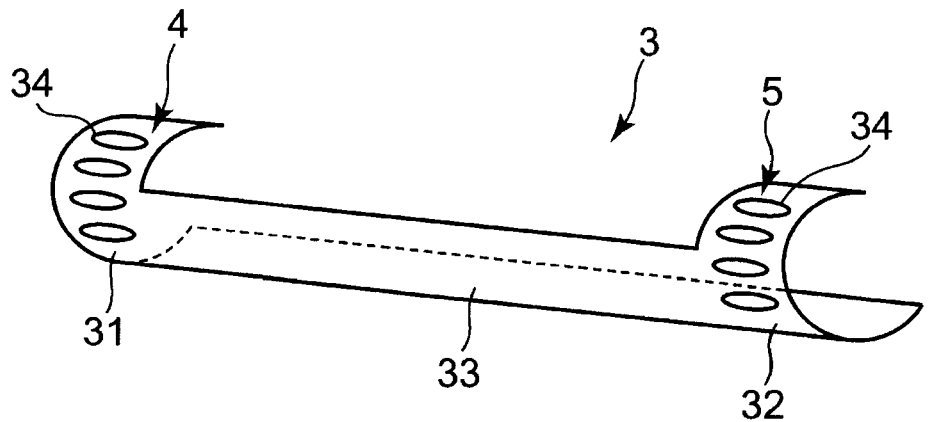
FIG. 9 is a perspective view of a puncture adapter in a second embodiment.

FIG. 9 is a perspective view of the puncture adapter 3 in the second embodiment. The second embodiment of the present invention is explained with reference to FIG. 9. It is the object of the present embodiment to easily turn the puncture adapter 3 comprising the guide portion 4, the operating portion 5, and the coupling portion 33, as is the case with the first embodiment.

As shown in FIG. 9, a plurality of elongated holes 34 are formed along the circumferential direction on the tubular component 31 of the guide portion 4 and the tubular component 32 of the operating portion 5. These elongated holes 34 act as a slip stopper between a hand and the guide portion 4 or the operating portion 5 when pinched by an operator, thereby enabling the operator to readily turn the puncture adapter 3. In addition, also when employing a clamp, they similarly act as a slip stopper. Moreover, a corrugated shape or a cutout may be used as such a slip stopper instead of the elongated holes 34. Alternatively, it may consist of at least one protrusion.

Herein, an example in which the guide portion 4 and the operating portion 5 are provided via the coupling portion 33 was shown in the abovementioned embodiment, but the present invention may include the case in which the abovementioned operating portion 5 and coupling portion 33 are absent. Hereinafter, the embodiment thereof is explained.

Figure 10A:
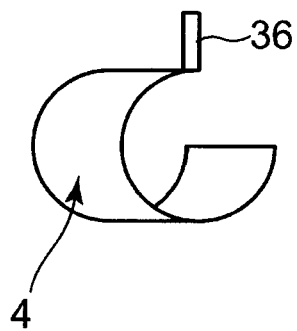
FIG. 10A is a perspective view of a puncture adapter in the second embodiment different from FIG. 9.
Figure 10B:
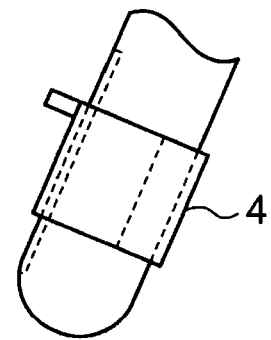
FIG. 10B is a view showing an ultrasonic probe on which the puncture adapter is mounted.

FIG. 10 shows an example of the puncture adapter 3 in which a protrusion 36 is provided on the guide portion 4. FIG. 10A is a perspective view of the puncture adapter 3, and FIG. 10B is a side view when the puncture adapter 3 is mounted on the insertion portion 10. As shown in FIG. 10B, the guide portion 4 is mounted so that the tip end of the insertion portion 10 covers a portion of the guide channel 11. In this case, operations such as a turn in the circumferential direction to the guide portion 4 can be performed by inserting a clamp via the trocar and pinching the protrusion 36 of the guide portion 4 within the abdominal area by employing a clamp that has been inserted.

Third Embodiment

The present embodiment is intended to facilitate the insertion of the puncture needle 2 to a guide opening formed by the guide channel 11 and the tubular component 31 of the guide portion 4.

Figure 11A:
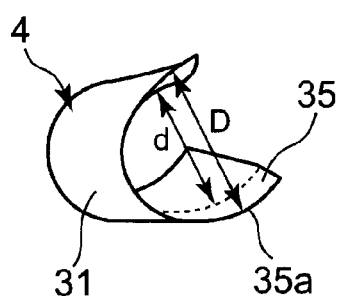
FIG. 11A is a perspective view of a puncture adapter in a third embodiment.
Figure 11B:
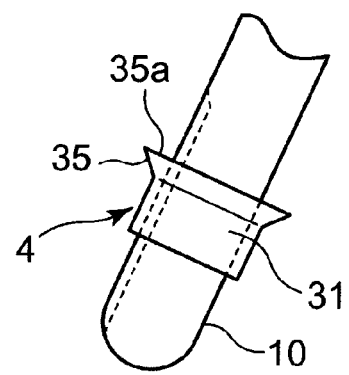
FIG. 11B is a view that shows an ultrasonic probe on which the puncture adapter is mounted.

FIG. 11A is a perspective view of the puncture adapter 3 in the third embodiment. FIG. 11B is a side view when the puncture adapter 3 in the third embodiment is mounted on the insertion portion 10.

As shown in FIG. 11A, the guide portion 4 consists of a tubular component 31 similar to that of the first embodiment. Then, among ends of the tubular component 31, an end 35a is the backside of the insertion portion 10 when mounted, and a sloped surface 35 is formed so that the diameter d of the opening of the tubular component 31 becomes larger up to the diameter D toward the end 35a. In other words, as shown in FIG. 11B, the guide portion 4 has the sloped surface 35 such as to separate from the surface of the insertion portion toward the backside of the insertion portion 10. Therefore, when piercing with the puncture needle 2 along the guide channel 11, the sloped surface 35 guides the tip of the puncture needle 2 to the guide opening formed by the guide channel 11 and the tubular component 31 of the guide portion 4. Thus, it becomes easier to insert the puncture needle 2 into the guide opening formed by the guide channel 11 and the tubular component 31 of the guide portion 4.

Fourth Embodiment

The present embodiment is intended to change the length of the guide opening formed by the guide channel 11 of the puncture needle 2 and the tubular component 31 of the guide portion.

Figure 12A:
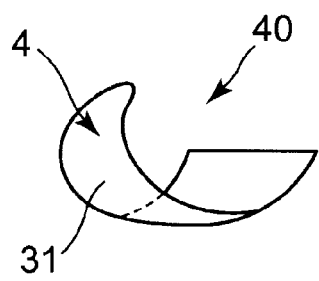
FIG. 12A is a perspective view of a puncture adapter in a fourth embodiment.
Figure 12B:
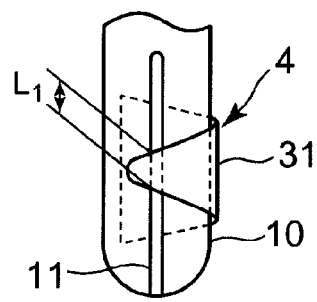
FIGS. 12B and 12C are views that show an ultrasonic probe on which the puncture adapter is mounted.
Figure 12C:
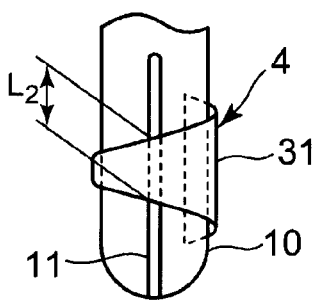

FIG. 12A is a perspective view of the puncture adapter 3 in the fourth embodiment. FIG. 12B and FIG. 12C are side views of the puncture adapter 3 in the fourth embodiment mounted on the insertion portion 10.

As shown in FIG. 12A, the guide portion 4 consists of a tubular component 31 similar to that of the first embodiment. Then, it is formed so that the width thereof changes, depending on the circumferential position of the cylinder. In the present example, the width of the tubular component 31 is adapted to gradually change from one end toward the other end of the gap 40. This makes it possible to change the length of the area that covers the guide channel 11, as shown in FIG. 12B and FIG. 12C. For example, the tubular component 31 of the guide portion 4 of FIG. 12B has a length L1 on the guide channel 11, but when further turning the puncture adapter 3, the tubular component 31 of the guide portion 4 has a length L2 on the guide channel 11 as shown in FIG. 12C. In this way, it is possible to change the length that covers the guide channel 11.

According to the puncture adapter and the ultrasonic probe in each embodiment described above, it is possible to cover the guide channel by turning the puncture adapter, and to form a guide opening for guiding the puncture by the puncture adapter and the guide channel. The guide opening allows the puncture needle to be stably guided or the puncture adapter is turned, locating the gap on the guide channel and opening the guide channel in order to enable the puncture needle to be easily detached from the guide channel.

What is claimed is:

1. An ultrasonic probe including an ultrasonic probe body and a puncture adapter, wherein
    the ultrasonic probe body comprises a rod shaped insertion portion insertable into a subject and a search unit for transmitting and receiving ultrasonic waves at a tip end of the insertion portion, and a guide channel for guiding a puncture needle being formed on a side surface of the insertion portion, and
    the puncture adapter comprises a first tubular component on which a gap is provided on a side surface thereof along a length direction, the gap extending from one end to an other end of the side surface, the first tubular component being mounted so as to contact an outside of the insertion portion and cover the guide channel, and being turnable in the circumferential direction thereof,
    wherein the first tubular component is a C-shaped structure which forms a C-shaped figure at the one end and the other end in a circumferential direction of the ultrasonic probe, and
    wherein the C-shaped structure covers the guide channel and the gap releases the guide channel when the puncture adapter is mounted on the ultrasonic probe.

2. The ultrasonic probe according to claim 1, wherein
    a width of the gap is at least wider than the guide channel, and
    the first tubular component detaches the puncture needle from the guide channel when the guide channel is placed into the gap by turning in the circumferential direction of the ultrasonic probe, and confines the puncture needle within the guide channel when the guide channels from the gap.

3. The ultrasonic probe according to claim 1, wherein a length from the one end to the other end of the first tubular component varies in the circumferential direction thereof.

4. The ultrasonic probe according to claim 1, wherein, when the first tubular component is mounted on the insertion portion, the diameter of a cross-section of the puncture adapter becomes larger toward a backside of the insertion portion.

5. The ultrasonic probe according to claim 1, wherein the first tubular component includes a plurality of cutouts, corrugated shapes or holes, or a protrusion along the circumferential direction thereof.

6. The ultrasonic probe according to claim 1, wherein the first tubular component consists of includes materials having springy characteristics.

7. The ultrasonic probe according to claim 1, wherein
    the puncture adapter is coupled with the first tubular component and further comprises a second tubular component having an opening, a cross-section of the opening being substantially circular, and
    the second tubular component contacts the outside of the insertion portion and is turnably mounted in the circumferential direction thereof along with the first tubular component.

8. A method for mounting a puncture adapter on an ultrasonic probe, the puncture adapter comprising a tubular component on which a gap is provided along a length direction thereof, the gap extending from one end to an other end of the tubular component, the ultrasonic probe comprising a rod shape insertion portion insertable into a subject and a search unit for transmitting and receiving ultrasonic waves at a tip end of the insertion portion, the ultrasonic probe in which a guide channel for guiding a puncture needle is formed on a side surface of the insertion portion, the method comprising:
    embedding the puncture adapter on an outside of the insertion portion from the gap of the tubular component,
    turning in the circumferential direction of the insertion portion to shift positions of the gap and the guide channel so as to cover the guide channel,
    allowing the puncture needle to pass through from the guide channel covered with the tubular component, and
    turning in the circumferential direction of the insertion portion after the puncture needle reaches a target area, to match the gap and the guide channel so that the puncture needle is detached from the guide channel,
    wherein the tubular component is a C-shaped structure which forms a C-shaped figure at the one end and the other end in a circumferential direction of the ultrasonic probe, and
    wherein the C-shaped structure covers the guide channel and the gap releases the guide channel when the puncture adapter is mounted on the ultrasonic probe.

* * * * *